(12) United States Patent
Niestroj-Pahl et al.

(10) Patent No.: US 10,383,605 B2
(45) Date of Patent: Aug. 20, 2019

(54) DEVICE FOR THE IN-VIVO AND/OR IN-VITRO ENRICHMENT OF TARGET STRUCTURES IN A SAMPLE LIQUID AND METHOD FOR THE PRODUCTION THEREOF

(71) Applicant: GILUPI GmbH, Potsdam (DE)

(72) Inventors: Robert Niestroj-Pahl, Potsdam (DE); Klaus Lücke, Potsdam (DE); Solveigh Krusekopf, Potsdam (DE); Frank Daniel Scherag, Freiburg (DE); Jürgen Rühe, Eichstetten (DE); Thomas Brandstetter, Freiburg (DE)

(73) Assignee: GILUPI GMBH, Potsdam (DE)

( * ) Notice: Subject to any disclaimer, the term of this patent is extended or adjusted under 35 U.S.C. 154(b) by 0 days.

(21) Appl. No.: 15/545,041

(22) PCT Filed: Jan. 20, 2016

(86) PCT No.: PCT/EP2016/051136
§ 371 (c)(1),
(2) Date: Jul. 20, 2017

(87) PCT Pub. No.: WO2016/116503
PCT Pub. Date: Jul. 28, 2016

(65) Prior Publication Data
US 2018/0008241 A1   Jan. 11, 2018

(30) Foreign Application Priority Data

Jan. 20, 2015 (DE) .......................... 10 2015 200 876

(51) Int. Cl.
*A61B 10/00*   (2006.01)
*G01N 33/543*   (2006.01)
(Continued)

(52) U.S. Cl.
CPC ...... *A61B 10/0045* (2013.01); *A61B 5/14503* (2013.01); *A61B 5/157* (2013.01);
(Continued)

(58) Field of Classification Search
CPC ............ A61B 10/0045; A61B 5/14503; A61B 5/150274; A61B 5/157; A61B 10/02;
(Continued)

(56) References Cited

U.S. PATENT DOCUMENTS

2012/0237944 A1   9/2012   Lucke et al.
2014/0357967 A1   12/2014   Lucke et al.

FOREIGN PATENT DOCUMENTS

CN   103691066 A   4/2014
EP   2807979 A1   12/2014
WO   2010145824 A1   12/2010

OTHER PUBLICATIONS

Islam et al., "Geometry Modeling of Screwed Wheel Dressed by Rounded Tool", Journal of the Chinese Society of Mechanical Engineers, 2015, pp. 283-290, vol. 36:4.

*Primary Examiner* — Melanie Brown
(74) *Attorney, Agent, or Firm* — The Webb Law Firm

(57) ABSTRACT

Device for the in-vivo and/or in-vitro enrichment of target structures in a sample liquid, including at least one functional portion, which is provided with receptors for enriching the target structures. In order to improve the enrichment of the target structures in the sample liquid, it is provided according to the invention that the functional portion has a helical shape, which is produced by twisting a symmetrical starting cross section about a twisting axis. The invention likewise discloses a method for producing this device.

16 Claims, 3 Drawing Sheets

(51) Int. Cl.
  *A61B 5/145* (2006.01)
  *A61B 5/15* (2006.01)
  *A61B 5/157* (2006.01)
  *A61B 10/02* (2006.01)
  *A61M 1/36* (2006.01)
  *G01N 33/00* (2006.01)

(52) U.S. Cl.
  CPC ........ *A61B 5/150274* (2013.01); *A61B 10/02* (2013.01); *A61M 1/36* (2013.01); *G01N 33/54366* (2013.01); *G01N 33/54393* (2013.01); *G01N 2033/0096* (2013.01)

(58) Field of Classification Search
  CPC .............. A61M 1/36; G01N 33/54366; G01N 33/54393
  See application file for complete search history.

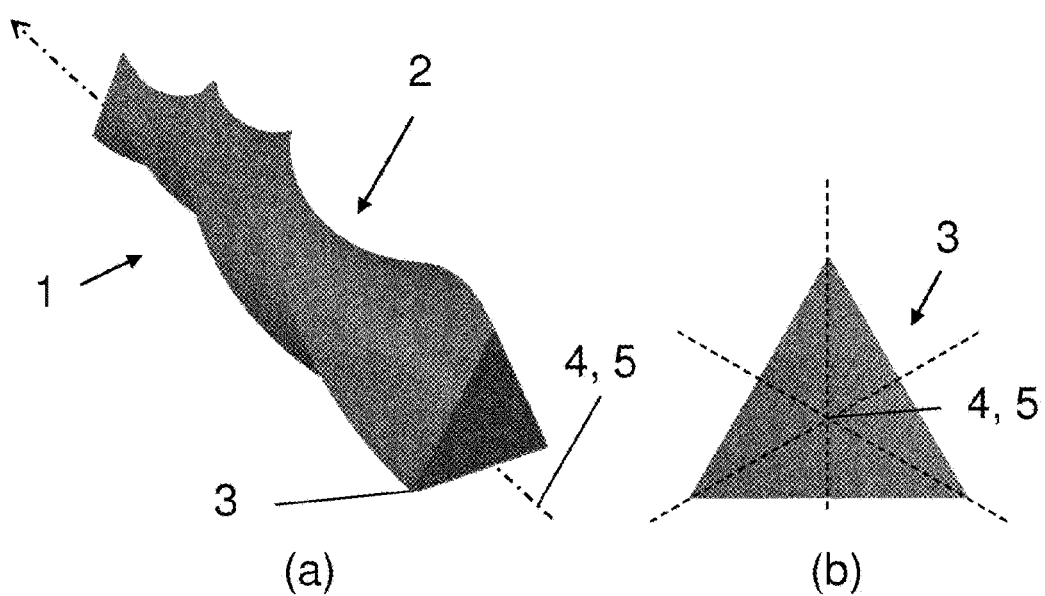
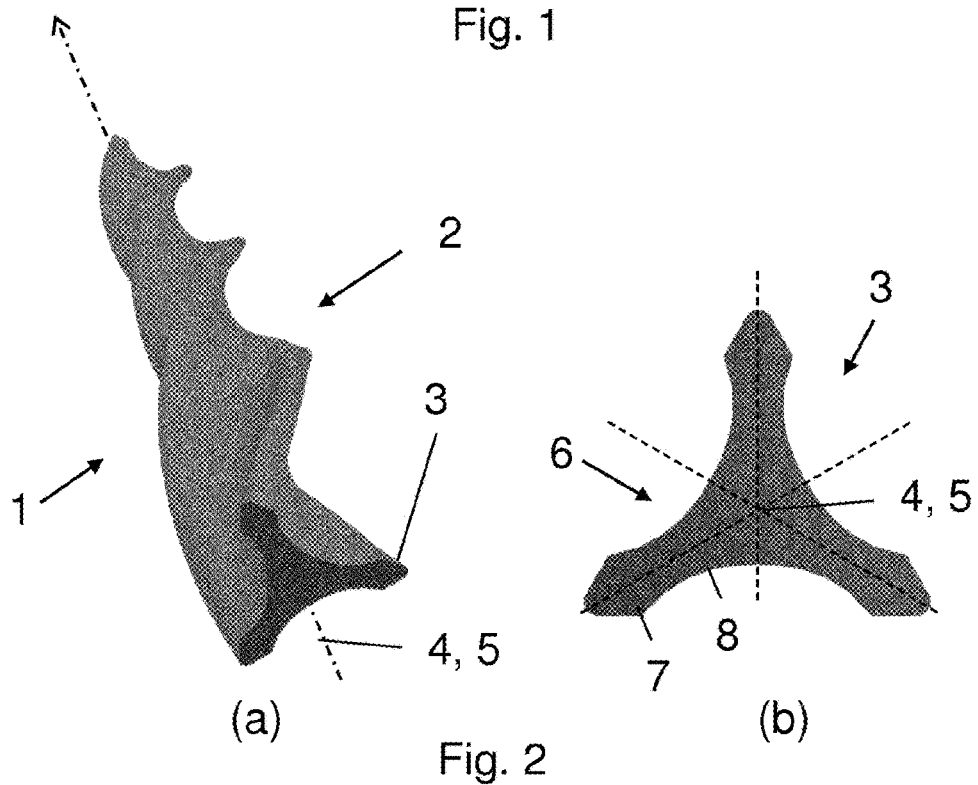
Fig. 1
Fig. 2

DEVICE FOR THE IN-VIVO AND/OR IN-VITRO ENRICHMENT OF TARGET STRUCTURES IN A SAMPLE LIQUID AND METHOD FOR THE PRODUCTION THEREOF

CROSS-REFERENCE TO RELATED APPLICATIONS

This application is the United States national phase of PCT International Application No. PCT/EP2016/051136 filed Jan. 20, 2016, and claims priority to German Patent Application No. 102015200876.2, filed Jan. 20, 2015, the disclosures of each of which is hereby incorporated by reference in their entireties.

BACKGROUND OF THE INVENTION

Field of the Invention

The invention relates to a device for the in-vivo and/or in-vitro enrichment of target structures in a sample liquid comprising at least one functional portion which is equipped with receptors for enriching the target structures. The invention also relates to a method for producing said device.

A device of the generic kind is known from WO 2010/145824 A1.

SUMMARY OF THE INVENTION

In some examples, provided herein is a device for the in-vivo and/or in-vitro enrichment of target structures in a sample liquid, comprising at least one functional portion which is equipped with receptors for enriching said target structures, wherein the functional portion has a helical shape, which arises by twisting a symmetrical starting cross-section about a twisting axis.

Also provided, in some examples, is a method for in-vivo and/or in-vitro enrichment of target structures in a sample liquid, comprising the steps of: a. providing the above-described device, b. introducing said functional portion into a sample liquid with a laminar flow, such that said twisting axis runs along or substantially along the direction of flow of said sample liquid, c. enriching said target structures in said sample liquid at the receptors of said functional portion, and d. removing said functional portion from said sample liquid.

In other examples, is a method for producing the above-described device, comprising the steps of: a. providing an elongate starting material having a symmetrical starting cross section over at least part of its length, where said elongate starting material preferably is a profiled wire, b. producing said functional portion by twisting at least a portion of the part of said elongate starting material having the symmetrical starting cross section about a twisting axis c. applying a coating onto said functional portion, d. binding receptors for enriching said target structures to said coated functional portion.

The invention is based on the object of improving the known device in order to improve the enrichment of the target structures in the sample liquid.

In order to satisfy the object, the invention provides a device for the in-vivo and/or in-vitro enrichment of target structures in a sample liquid, comprising at least one functional portion which is equipped with receptors for enriching the target structures, where the functional portion has a helical shape, which arises by twisting a symmetrical starting cross section about a twisting axis. The device is introduced into a laminar flow, such as, for example, into a bloodstream system and there creates a transverse flow which leads to turbulences of the sample liquid and the target structures contained therein in the region of the surface of the functional portion which is equipped with the receptors. As a result, a markedly improved enrichment of the target structures at the receptors of the functional portion is possible in this manner.

It can be advantageous if the starting cross section has at least one of the following features:

The starting cross section is mirror-symmetrical, preferably many-fold mirror-symmetrical.

The starting cross section is rotationally symmetrical with respect to an axis of rotation, is preferably many-fold rotationally symmetrical, preferably at least two, three, four or five-fold rotationally symmetrical. The rotational symmetry (or radial symmetry) is a form of symmetry in which the rotation of the starting cross section by a certain angle about an axis of rotation brings this starting cross section to again coincide with itself. This axis of rotation preferably runs through the center of area of the starting cross section. An n-fold radial or rotational symmetry is given when a rotation by 360°/n maps the starting cross section onto itself. For example, equilateral triangles (cf. the first starting example) are three-fold in their rotational symmetry and have an axis of symmetry perpendicular to the triangle plane which, when rotated by 120° and 240°, maps it onto itself.

The starting cross section is a polygon or is based on a polygon, preferably an equilateral and/or equiangular polygon, preferably a 3-gon (trigon), 4-gon (tetragon), 5-gon (pentagon), 6-gon (hexagon), 7-gon (heptagon), 8-gon (octagon), 9-gon (nonagon, enneagon), 10-gon (decagon), 11-gon (hendecagon) or 12-gon (dodecagon). Such cross sectional shapes are particularly symmetrical and enhance the flow in a flow system.

At least one side of the starting cross section has a convex or concave curvature. As a result, the turbulence can be increased and the surface area of the functional portion can be further enlarged.

The starting cross section is convex (all internal angles are less than 180°) or concave or non-convex (at least one internal angle is greater than 180°), respectively, preferably several fold concave (at least two internal angles are greater than 180°), preferably three-fold, four-fold, five-fold, six-fold concave (three, four, five or six internal angles are greater than 180°).

The starting cross section is triangular, rectangular or star-shaped. A triangular starting cross section has proven to be particularly advantageous in experiments.

At least one corner of the starting cross section is rounded. This serves to prevent damage to the vessel of the sample liquid or to potential weak spots in the material.

The starting cross section becomes smaller or larger while the cross sectional shape along the twisting axis remains the same.

The starting cross section comprises at least one arm preferably extending along a line when starting out from the axis of rotation, where the arm preferably comprises at least one thickening and/or at least one taper, where the line particularly preferably extends radially relative to the axis of rotation or is curved with respect to a radial to the axis of rotation. Such an arm forms an extension which creates a relatively large surface while having a comparatively small cross sectional area when twisted about the twisting axis. The arm is preferably rounded at the free end in order to avoid damage to the vessel of the sample liquid.

The starting cross section is created by a subsequent intersection of the helical shape with a geometric body, in particular a body which is rotationally symmetrical with respect to the twisting axis, such as, for example, a cone. If, for example, the helical shape is subsequently cut with a coaxial conical shell so that all parts of the helical shape located outside the conical shell are removed, a spatially complex shape can be obtained in which the functional portion, for example, becomes smaller or larger towards one end, whereas the helical shape in the interior remains. Such a structure can lead to the fact that the flow portions of the sample liquid separated by the functional portion are again united downstream of the functional portion in a manner largely without disturbance.

It can also be advantageous if the helical shape has at least one of the following features:

The twisting axis is simultaneously the axis of rotation. Accordingly, the rotationally symmetrical starting cross section is twisted about itself. This embodiment promotes the formation of laminar transverse flows in the flow system of the sample liquid.

The twisting axis is located within the starting cross section, where the twisting axis preferably runs through the center of area of the starting cross section or runs outside the center of area of the starting cross section. The first preferred variant, in which the twisting axis runs through the center of area of the starting cross section, creates comparatively compact twisting structures. The second preferred variant, in which the twisting axis runs outside the center of area of the starting cross section, creates more voluminous structures having a larger surface area.

The twisting axis is located outside the starting cross section. In this variant, helical twisting structures can be created which keep a central flow cross section clear along the twisting axis.

The lead is at most 20 mm, preferably at most 5 mm. The number of turns is therefore preferably 0.2 turns per millimeter. With such a lead or number of windings, ideal flow conditions can be created in a bloodstream system having the usual flow conditions.

The helical shape has a constant lead. This embodiment promotes the formation of a laminar transverse flow in a flow system and facilitates the production of the device.

The helical shape has a constant pitch. This embodiment also facilitates the production of the device and can further improve the flow conditions in a flow system.

The helical shape has a constant radius. This embodiment also facilitates the production and can provide optimum flow conditions in a flow system.

It can prove to be practical if the functional portion has at least one of the following features:

The functional portion comprises a maximum diameter of 3 mm. The minimum diameter is limited by manufacturing technology and by the respective material properties. Such dimensions are optimized for blood vessels and can be introduced into a bloodstream, for example, through a peripheral venous catheter.

The functional portion comprises a length of 10 to 200 mm. This length range is particularly suitable for the formation of a functional surface equipped with receptors.

The functional portion is located at the leading or free (distal) end of the device and/or forms the leading or free (distal) end of the device, respectively. Preferably, only the functional portion is introduced into the bloodstream of a patient in order to come into direct contact with blood so that the target structures can be enriched at the receptors.

The functional portion is made of biocompatible and easily processed material, for example metal, preferably medical stainless steel, an optical or other polymer, for example, poly (methyl methacrylate) (PMMA), or ceramic material. The material properties of these materials are suitable for the production and application of the device according to the invention.

The functional portion is flexible and/or elastic, preferably resiliently flexible. Such material properties are particularly desirable in order to be able to introduce the functional portion into the bloodstream of a patient through a peripheral venous catheter system. Due to the flexibility and/or elasticity, the functional portion can follow the shapes of the blood vessel, thereby reducing the risk of injury to the patient and facilitating handling of the device.

The functional portion comprises a coating which follows the contour of the functional portion. The coating is preferably so thin that the helical shape of the functional portion is not significantly altered by the coating. Accordingly, the coated functional portion preferably also has the same helical shape as the uncoated functional portion.

The coating of the functional portion is biocompatible and/or blood-repellent. Such a coating leads to no blood constituents being retained on the coating, with the exception of the desired target structures.

The coating of the functional portion is a polymer, preferably a hydrogel, preferably a crosslinked hydrogel. A hydrogel has a branched surface structure which can significantly improve binding the desired receptors as well as binding the desired target structures to the bound receptors.

A further aspect of the present invention relates to the use of the device according to one of the preceding claims for the in-vivo and/or in-vitro enrichment of target structures in a sample liquid comprising the steps of:

introducing the functional portion into a sample liquid with a laminar flow, preferably into a bloodstream, such that the twisting axis runs along or substantially along the direction of flow of the sample liquid. The functional portion is preferably brought into the bloodstream of a patient through a peripheral venous catheter in order to come into direct contact with the patient's blood. The functional portion then extends along the blood vessel and the patient's blood flows around it. The helical structure of the functional portion acts as a static mixer and causes turbulence that intermix the target structures within the sample liquid and significantly increase the likelihood of random contact with receptors immobilized on the functional portion.

enriching the target structures in a sample liquid at the receptors of the functional portion. This enrichment of the target structures at the receptors of the functional portion is significantly increased by the helical contour of the functional portion in the flow system of the human bloodstream due to the flow effects mentioned.

removing the functional portion from the sample liquid. Removal of the functional portion from the sample liquid preferably occurs after a residence time of approximately 30 minutes in the bloodstream of the patient. The analysis of the target structures enriched at the receptors preferably occurs outside the sample liquid.

Yet another aspect of the present invention relates to a method for producing the device according to any one of the preceding claims, comprising the steps of:

providing an elongate starting material having a symmetrical starting cross section over at least part of its length, where the elongate starting material preferably is a profiled wire. A wire with a specific profile (for example, a flat wire or a triangular profile) can be produced inexpensively from metal in an extrusion process. This profiled wire can serve as a starting material for subsequent processing. However, it is also possible to use a profiled wire made of plastic material or other suitable materials.

producing the functional portion by twisting at least a portion of the part of the elongate starting material having the symmetrical starting cross section about a twisting axis. For this purpose, preferably one end of the wire is clamped and another end of the wire is twisted. The twisting axis preferably coincides with the center of area of the starting cross section or the longitudinal axis of the wire, respectively. Alternatively, it is possible to wind the wire around a cylindrical or conical element such that the wire assumes a helical shape which is defined by the circumferential surface of the cylindrical or conical element. In this case, the twisting axis is located outside the starting cross section.

applying a coating onto the functional portion. The interactions with the sample liquid and the target structures contained therein can be selectively adjusted by way of the coating of the functional portion. The coating can have less than one layer. It is preferably a multilayer system, as described, for example, in WO 2010/145824 A1.

binding receptors for enriching the target structures to the coated functional portion. The receptors are preferably antibodies which are preferably covalently bound to the coating, in particular, hydrogel. Binding these receptors to the coating is also described in detail in WO 2010/145824 A1.

The production method can comprise at least one further method step which leads to the production of at least one present feature of the device according to one of the above embodiments.

BRIEF DESCRIPTION OF THE DRAWINGS

The foregoing summary, as well as the detailed description, will be better understood when read in conjunction with the appended drawings. The present invention is described herein in greater detail using an embodiment and associated drawings. In the drawings:

FIG. 1 (*a*) shows a perspective view of the functional portion of a device for in-vivo and/or in-vitro enrichment of target structures in a sample liquid according to the first embodiment of the invention, where the helical functional portion has a shape which is obtained by twisting the starting cross section shown in (*b*) in the form of an equilateral triangle along the twisting axis.

FIG. 2 (*a*) shows a perspective view of the functional portion of a device for in-vivo and/or in-vitro enrichment of target structures in a sample liquid according to the second embodiment of the invention, where the helical functional portion has a shape which is obtained by twisting the mirror-symmetrical and 3-fold rotationally symmetrical starting cross section shown in (*b*) along the twisting axis.

DETAILED DESCRIPTION

Figure 3:
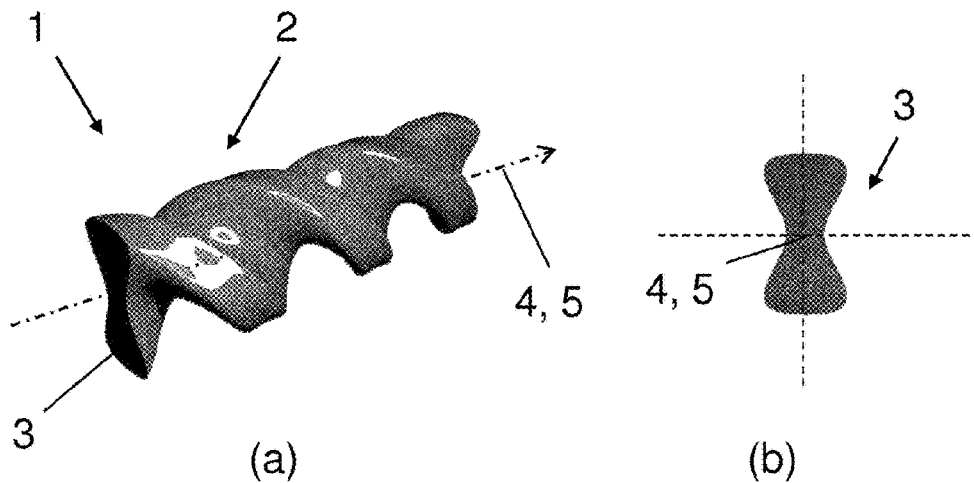
FIG. 3 (*a*) shows a perspective view of the functional portion of a device for in-vivo and/or in-vitro enrichment of target structures in a sample liquid according to the third embodiment of the invention, where the helical functional portion has a shape which is obtained by twisting the twice mirror-symmetrical and 2-fold rotationally symmetrical starting cross section shown in (*b*) along the twisting axis.

The preferred embodiments of the invention are described below with reference to the appended figures:

The invention describes a device based, for example, on a catheter, a stent, a guide wire or the like, for the in-vivo application in humans for the enrichment of target structures from body liquids, in particular from the bloodstream. Of course, the device can also be used outside the human body (in-vitro). This is a further development of the invention that is described in the international patent application WO 2010/145824. The contents of WO 2010/145824 A1 are by reference incorporated herein in their entirety.

Within the scope of this invention, the detection device described in WO 2010/145824 A1 is supplemented by a differently structured functional portion. The underlying structure of the detection device described in WO 2010/145824 A1 is maintained.

According to the present invention, the functional portion is a helically wound element which can be wound around its own (torsion) or in a defined perimeter about an axis. It has been found that structures twisted about themselves and about an axis increase the detection rate for target structures, irrespective of the detection receptors. It has been found that, due to the above-mentioned twisting:

1. the three-dimensional structures produce a disturbance of the laminar flow when used in a blood-carrying vessel, whereby target particles enter the inner space of the structure defined by the facing surfaces, thereby increasing the contact likelihood of structures from the blood with the functional element.
2. the structured functional portion between the facing surfaces forms an "inner space" consisting of preferably concavely shaped regions as large as possible with a flow velocity reduced due to structural reasons, where the shear stress arising on contact of the target structures with the functional portion is reduced and the attachment likelihood is thereby increased. The helical inner space formed by definition increases the likelihood of contact between the target structures entering the inner region and the functional portion because these target structures are highly likely to impinge on the helical structure due to the main flow direction running parallel to the venous wall. Furthermore, the inner space formed by definition provides the bound target structures with protection against abrasion when the detection device is removed from the body.
3. the surface area of the functional element is increased.

The advantage over, for example, a cylindrical structure is the intermixing of the blood present in the laminar flow. This is caused by the helical structure already described in WO 2010/145824 A1 and exhibits the principle of a "static mixer" The shape of a static mixer causes intermixing of the blood flowing past and thus an increased likelihood of collision of target structures with the functional portion. The surface area of the functional portion enlarged by the helical shape also increases the likelihood of contacts of target structures.

Possible embodiments for functional portions created by torsion have, for example, triangular or rectangular starting cross sections. The functional portion can be configured as a triangular bar or as a flat bar, preferably with a mill edge, and can be twisted. The polygonal cross section can have a hollow shape on the longitudinal sides.

The functional portion can be made of metal, plastic or ceramic material, preferably medical stainless steel, or an optical polymer.

The functional portion can be provided with a functional blood-repellent coating, as already described in WO 2010/145824 A1, to which the detection receptors can be bound. The coating can be made of a synthetic or natural polymer or copolymer, which preferably contains carboxyl groups as functional groups. The polymer is preferably crosslinked and can be bound to the surface of the functional element by way of a bonding agent. The combination of two polymers, such as e.g. polyelectrolytes, of natural or synthetic origin is also possible, which form one (monolayer) or several layers (multilayer).

In the context of this invention, the detection device is simply referred to as a device.

Device 1 is based on a wire having a length of 100-200 mm. Located at the distal end of the wire is said functional portion 2, the surface of which is functionalized with receptors for target structures. Functional portion 2 comprises a diameter of up to a maximum of 3 mm, the minimum diameter is determined by technical possibilities and material properties and should be as small as possible. The functional portion has a length of 10 to 200 mm. Functional portion 2 is preferably made of metal, preferably medical stainless steel, of ceramic material or an optical or other polymer, preferably PMMA, and can be provided with a blood-repellent layer for coupling of receptors, which can be a hydrogel or a functional polymer or copolymer.

First Embodiment (FIGS. 1 (a) and (b))

In the first embodiment according to FIG. 1, device 1 is based on a triangular wire. Functional portion 2 has a helical shape which is created by twisting starting cross section 3, having the shape of an equilateral triangle, along linear twisting axis 4. The equilateral triangle is an example of a three-fold rotationally symmetrical starting cross section 3 which is mapped upon itself by rotation about 120° and 240° about an axis of rotation 5 coinciding with twisting axis 4. The corners of starting cross section 3 can additionally be rounded in order to reduce the risk of injury.

Second Embodiment (FIGS. 2 (a) and (b))

In the second embodiment according to FIG. 2, the wire, in deviation from the first exemplary embodiment according to FIG. 1, has additional indentations on the sides of the triangle and is rounded at the corners. Each indentation provides a larger inner space for binding target structures As is evident from FIG. 2(b), starting cross section 3 comprises a total of three arms 6, each extending in the radial direction from axis of rotation 5 that coincides with twisting axis 4, and a taper 8 arranged between thickening 7 and axis of rotation 5. Starting cross section 3 is mirror-symmetrical and rotationally symmetrical with respect to axis of rotation 5.

Third Embodiment (FIGS. 3 (a) and (b))

The third embodiment according to FIG. 3 is based on twisting a flat wire which substantially has a starting cross section 3 in the form of a bone. A rounded flat wire can be produced by pressing a round wire smooth, creating a so-called mill edge. The flat wire can be planar or additionally have a concave indentation in the middle. A larger inner space for binding target structures is created by the additional indentation. Starting cross section 3 is twice mirror-symmetrical and 2-fold rotationally symmetrical with respect to axis of rotation 5. The curvature of the arms is preferably in the twisting direction.

Figure 4:
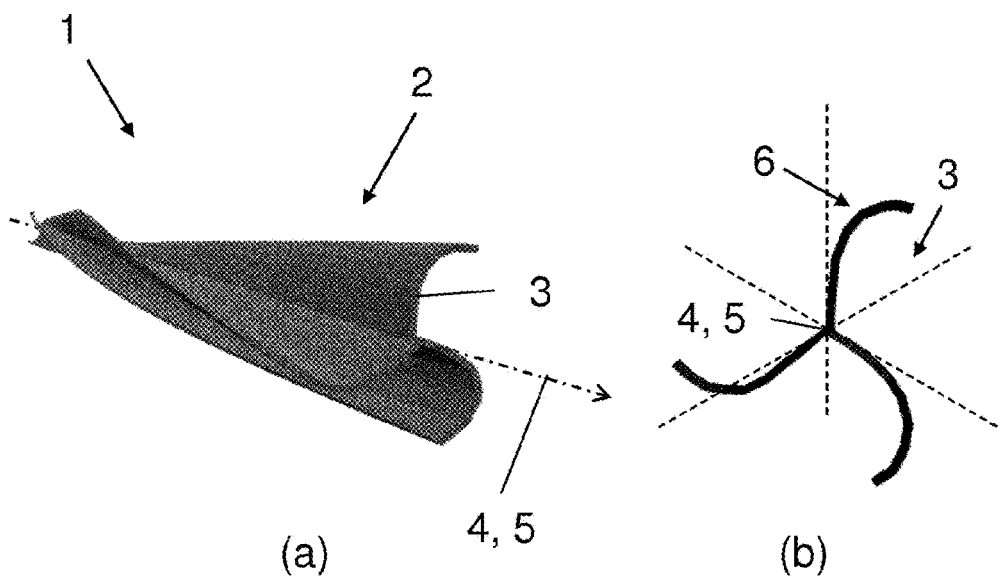
FIG. 4 (*a*) shows a perspective view of the functional portion of a device for in-vivo and/or in-vitro enrichment of target structures in a sample liquid according to the fourth embodiment of the invention, where the helical functional portion has a shape which is obtained by twisting a starting cross section having the shape of the three-arm and three-fold rotationally symmetrical—but not mirror-symmetrical—starting cross section shown in (*b*) along the twisting axis.

Fourth Embodiment (FIGS. 4 (a) and (b))

The fourth embodiment according to FIG. 4 is based substantially on a three-armed starting cross section 3, the three arms 6 of which initially extend radially from axis of rotation 4 coinciding with twisting axis 4 and are curved at the free end with respect to a radial to axis of rotation 5. With this shape, the inner space of the functional surface is enlarged and liquid-conducting channels are formed more pronounced. This starting cross section 3 is not mirror-symmetrical due to the one-sided curvatures of arms 6, but 3-fold rotationally symmetrical with respect to axis of rotation 5.

Figure 5:
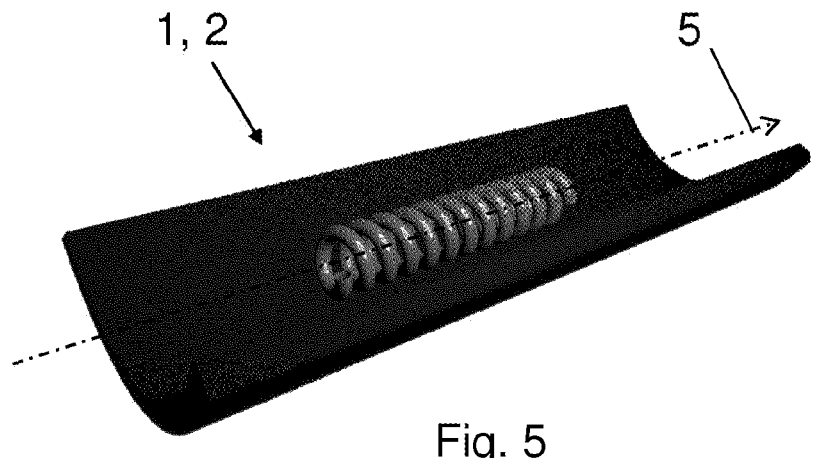
FIG. 5 (on a trough-shaped support which is not part of the invention) shows a perspective view of the functional portion of a device for the in-vivo and/or in-vitro enrichment of target structures in a sample liquid according to the fifth embodiment of the invention, where the functional portion has the shape of a cylindrical helix which is obtained by twisting a circular starting cross section along an eccentric twisting axis, where the helix has a constant pitch and lead.
Figure 6:
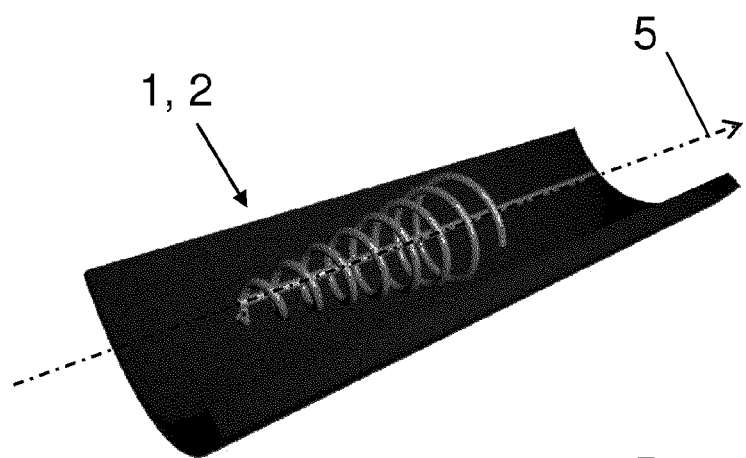
FIG. 6 (on a trough-shaped support which is not part of the invention) shows a perspective view of the functional portion of a device for the in-vivo and/or in-vitro enrichment of target structures in a sample liquid according to the sixth embodiment of the invention, where the functional portion has the shape of a conical helix which is obtained by twisting a circular starting cross section along an eccentric twisting axis, where the helix has a constant lead while the radius reduces and a pitch increasing toward the tip of the cylinder.
Figure 7:
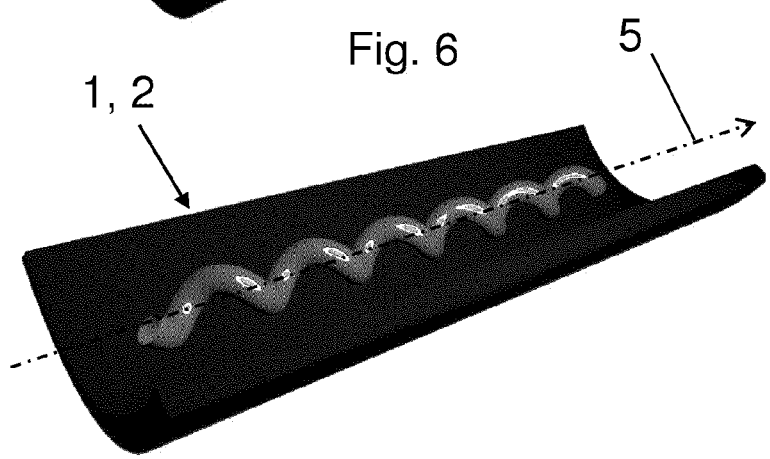
FIG. 7 (on a trough-shaped support which is not part of the invention) shows a perspective view of the functional portion of a device for the in-vivo and/or in-vitro enrichment of target structures in a sample liquid according to the seventh embodiment of the invention, where the functional portion has the shape of a cylindrical helix which is obtained by twisting a circular starting cross section along an eccentric twisting axis, where the cylindrical helix has a lead that is larger and a radius that is smaller as compared to the fifth embodiment.

Embodiments Five, Six and Seven (FIGS. 5 to 7)

In embodiments five, six and seven according to FIGS. 5-7, functional portion 2 is formed as a spiral, straight or tapering to a tip, and having a different pitch. Devices 1 are each shown on a trough-shaped support which is not part of the object of the invention.

Although the device is designed and dimensioned primarily for being used for the enrichment of target structures in the human bloodstream (in-vivo), it is understood that the device can also be used outside the human body (in-vitro).

LIST OF REFERENCE NUMERALS

1: device
2: functional portion
3: starting cross section
4: twisting axis
5: axis of rotation
6: arm
7: thickening
8: taper

The invention claimed is:

1. A device for the in-vivo and/or in-vitro enrichment of target structures in a sample liquid, comprising at least one functional portion which is equipped with receptors for enriching said target structures, wherein the functional portion has a helical shape, which arises by twisting a symmetrical starting cross-section about a twisting axis, wherein the starting cross section is a concave polygon.

2. The device according to claim 1, wherein the starting cross section is mirror-symmetrical and/or rotationally symmetrical with respect to an axis of rotation.

3. The device according to claim 2, wherein the starting cross section is many-fold rotationally symmetrical with respect to the axis of rotation.

4. The device according to claim 1, wherein the starting cross section is at least two, three, four or five-fold rotationally symmetrical with respect to the axis of rotation.

5. The device according to claim 1, wherein the starting cross section comprises at least one arm.

6. The device according to claim 5, wherein the at least one arm extends along a line when starting out from said axis of rotation.

7. The device according to claim 6, wherein said arm comprises at least one thickening and/or at least one taper.

8. The device according to claim 6, wherein said line extends radially relative to said axis of rotation or is curved with respect to a radial to said axis of rotation.

9. The device according to claim 1, wherein the said twisting axis is simultaneously an axis of rotation.

10. The device according to claim 1, wherein the twisting axis is located within said starting cross section.

11. The device according to claim 10, wherein the twisting axis runs through the center of area of said starting cross section.

12. The device according to claim 1, wherein the twisting axis is located outside said starting cross section.

13. The device according to claim 1, wherein the helical shape has a constant lead and/or a constant pitch and/or a constant radius.

14. The device according to claim 1, where said polygon is concave, wherein at least one internal angle is greater than 180°, or where at least one side of said polygon has a concave curvature.

15. A method for in-vivo and/or in-vitro enrichment of target structures in a sample liquid, comprising the steps of:
 a. providing a device according to claim 1,
 b. introducing said functional portion into a sample liquid with a laminar flow, such that said twisting axis runs along or substantially along the direction of flow of said sample liquid,
 c. enriching said target structures in said sample liquid at the receptors of said functional portion, and
 d. removing said functional portion from said sample liquid.

16. A method for producing the device of claim 1, comprising the steps of:
 a. providing an elongate starting material having the concave polygon starting cross section over at least part of its length, where said elongate starting material,
 b. producing said functional portion by twisting at least a portion of the part of said elongate starting material having the the concave polygon starting cross section about a twisting axis,
 c. applying a coating onto said functional portion, and
 d. binding receptors for enriching said target structures to said coated functional portion.

* * * * *

UNITED STATES PATENT AND TRADEMARK OFFICE
CERTIFICATE OF CORRECTION

PATENT NO.       : 10,383,605 B2
APPLICATION NO.  : 15/545041
DATED            : August 20, 2019
INVENTOR(S)      : Robert Niestroj-Pahl et al.

It is certified that error appears in the above-identified patent and that said Letters Patent is hereby corrected as shown below:

In the Claims

Column 10, Line 37, Claim 16, delete "the the concave polygon" and insert -- the concave polygon --

Signed and Sealed this
Twelfth Day of November, 2019

Andrei Iancu
*Director of the United States Patent and Trademark Office*